United States Patent [19]
Campbell et al.

[11] Patent Number: 5,888,744
[45] Date of Patent: Mar. 30, 1999

[54] DETECTION AND SEPARATION OF AMINOGLYCOSIDES BY BINDING TO IMMOBILIZED LYSOZYME OR α-LACTALBUMIN

[75] Inventors: Naomi F. Campbell, Mobile, Ala.; Marjorie B. Medina, Glenside, Pa.

[73] Assignee: The United States of America, as represented by the Secretary of Agriculture, Washington, D.C.

[21] Appl. No.: 518,869

[22] Filed: Aug. 24, 1995

[51] Int. Cl.$^6$ .......................... G01N 33/53; G01N 33/04; C12N 11/08; C07H 1/06

[52] U.S. Cl. .............................. 435/7.1; 435/7.5; 435/7.9; 435/18; 435/180; 530/815; 536/22.1; 536/127; 436/22

[58] Field of Search .............................. 435/174, 7.1, 7.5, 435/7.92, 18, 25, 26, 28, 4, 7.9, 180; 536/22.1, 124, 127; 530/815; 436/22

[56] References Cited

U.S. PATENT DOCUMENTS

| | | | |
|---|---|---|---|
| 4,181,636 | 1/1980 | Fischer | 260/8 |
| 4,328,311 | 5/1982 | Rowley et al. | 435/188 |
| 4,340,736 | 7/1982 | Facella et al. | 544/301 |
| 4,482,707 | 11/1984 | Sakakibara et al. | 536/14.8 |
| 4,693,985 | 9/1987 | Degan et al. | 436/531 |
| 4,729,951 | 3/1988 | Ferenczy et al. | 435/80 |
| 4,990,442 | 2/1991 | Del Campo | 435/7.5 |
| 5,310,565 | 5/1994 | Geyer | 426/271 |

OTHER PUBLICATIONS

Bishop et al., "Detection of Antibiotic/Drug Residues in Milk and Dairy Products", *Standard Methods for the Examination of Dairy Products*, 16th ed., R.T. Marshall, Ed., American Public Health Assoc., Wash. DC.

Yao et al, "Enzyme–Linked Immunosorbent Assay for the Detection of Fermentation Meltabolites: Aminoglycoside Antibiotics", *The Journal of Antibiotics*, vol. xxxvii, No. 11, pp. 1462–1468, 1984.

Haagsma et al., "High–Performance Liquid Chromatographic Determination of Spectinomycin in Swine, Calf and Chicken Plasma", *J. of Chromatography*, vol. 615, pp. 289–295 (1993).

Tsuji et al., "Derivatization of Secondary Amines with 2–Naphtalene–Sulfonyl Chloride . . . ", *J. of Chromatography*, vol. 333, pp. 365–380 (1985).

Medina et al., "Solid Phase Clean–up and TLC Analysis of Hygromycin B in Bovine Plasma and Swine Serum", in: *Residues of Verterinary Drugs in Food*, Proceedings of the EuroResidue II Conference, Edited by Haagsma et al., 1993.

Maron et al., "Immunological Studies of Affinity Labelled Hen Egg–White Lysozyme and of the Active Site Region of Related Lysozymes", *Biochimica Et Biophysica Acta*, vol. 278, pp. 243–249 (1972).

Hancock et al., "Interaction of Aminoglycosides with the Outer Membranes and Purified Lipopolysaccharide and OmpF Porin of Escherichia coli", *Ant. Agents and Chem.*, pp. 1309–1314 (1991).

Medina and Unruh, "Solid–Phase Clean–Up and Thin–Layer Chromatographic Detection of Veterinary Aminoglycosides", *J. of Chromatography B*, vol. 663, pp. 127–135 (1995).

Shaikh and Allen, "Overview of Physical–Chemical Methods . . . ", *J. Assoc. Off. Anal. Chem.*, vol. 68, No. 5, pp. 1007–1013 (1985).

Medina, "A Competitive Protein Binding Assay for Spectinomycin using Particle Concentration Flourescent Assay", Abstract Index, 108th AOAC International Meeting and Exposition, Portland, Oregon, Sep. 12–15, 1994.

Lai and Sheehan, "Matrix Effects in the Deriviation of Amino Acids . . . ", *Bio Techniques*, vol. 14, No. 4, pp. 642–649 (1993).

Maitra et al.,"Determination of Aminoglycoside Antibiotics . . . ", *Clin. Chem.*, vol. 25(8), pp. 1361–1367 (1979).

Fernandez–Sousa et al., "On the Inhibition of Hen Egg–White Lisozyme Activity . . . ", *Biochem. and Biophy. Res. Com.*, vol. 75(4), pp. 895–890 (1977).

Scheurer and Moore, "Solid–Phase Extraction of Drugs from Biological Tissues", *J. of Anal. Toxi.*, vol. 15, pp. 264–269 (1992).

Jehl et al., "High–Performance Liquid Chromatography of Antibiotics", *J. of Chrom. B*, vol. 531, pp. 509–548 (1990).

Sharon and Eshdat, "Affinity Labeling of Lysozyme", Chapter 18, pp. 195–218.

Evangelista and Chen, "Analysis of structural specificty in antibody–antigen reactions . . . ", *J. of Chromatography A.*, vol. 680, pp. 587–591 (1994).

Fägerstam, L., "A Non–Label Technology for Real–Time Biospecific Interaction Analysis", Article submitted for publication in: *Techniques in Protein Chemistry II*, Vilanfranca, J.J. (ed.), Academic Press, New York (1990).

Medina, J., *J. Aric. Food Chem.*, vol. 34(6), pp. 1046–1049 (1986).

*Primary Examiner*—David M. Naff
*Attorney, Agent, or Firm*—M. Howard Silverstein; John Fado; Gail E. Poulos

[57] ABSTRACT

Aminoglycosides such as aminoglycoside antibiotics are detected and separated by non-immunoaffinity binding to an immobilized binding protein which is preferably lysozyme or α-lactalbumin. Aminoglycosides are detected in a biological sample such as milk or a fermentation broth by contacting the sample with the binding protein immobilized on a solid carrier such as particles of carboxylated latex to bind the aminoglycosides to the binding protein, adding a label that binds to the aminoglycosides and measuring the label. In another embodiment, the binding protein containing bound aminoglycosides is separated from the sample, the aminoglycosides are removed from the binding protein, a label is added to the aminoglycosides and the label is measured. Aminoglycosides are removed from a sample by passing the sample through a bioreactor containing the binding protein immobilized on a solid carrier to bind the aminoglycosides to the binding protein and recovering the sample free of aminoglycosides. The immobilized binding protein with bound aminoglycosides may be removed from the bioreactor and the aminoglycosides eluted from the binding protein.

11 Claims, 10 Drawing Sheets

DETECTION AND SEPARATION OF AMINOGLYCOSIDES BY BINDING TO IMMOBILIZED LYSOZYME OR α-LACTALBUMIN

BACKGROUND OF THE INVENTION

1. Field of the Invention

The present invention relates to a non-immunoaffinity binding method for the detection and assay of aminoglycoside antibiotics in foods of animal origin using lysozyme and α-lactalbumin as the binding proteins. It also relates to the purification of aminoglycosides from biological fluids such as fermentation broths and to the purification of biological fluids such as milk.

2. Description of the Prior Art

The aminoglycoside antibiotics consist of a group of related antibiotics containing aminosugar residues. The primary effect of the aminoglycoside antibiotics is the inhibition of protein synthesis (Wilhelm et al, Biochem. Vol. 17, 1149–1153, 1978; Wilhelm et al, Biochem., Vol. 17, 1143–1149, 1978). Some of these antibiotics have been approved as a feed additive to control parasitic, respiratory and enteric infections in farm animals. Therefore, rapid methods are needed to screen for the presence of trace levels of these class of antibiotics in biological fluids and tissues. Hygromycin B inhibits the growth of microorganisms and mammalian cells and is used to control parasitic, respiratory and enteric infections in poultry and swine. Residues from hygromycin B may occur in tissues and fluids of farm animals designated for human consumption. Spectinomycin hydrochloride is allowed for treatment and control of bacterial enteritis in swine and in the prevention and control of losses due to chronic respiratory disease associated with *M. gallisepticum* (PPLO) in poultry. The tolerance for spectinomycin residue is 0.1 ppm in the uncooked edible tissues of chickens. Neomycin residues in eggs are quite stable to normal egg preparation procedures. Frying eggs causes little or no loss of activity, poaching results in a 25% loss, and soft boiling and hard boiling causes little or no loss of activity. Antibiotics administered to dairy cattle whether applied by infusion, injection or oral means, sometimes enters the milk supply. This presence of antibiotics in milk, at the consumer level, can cause allergic reactions, affect starter cultures, or create environments favorable for resistant bacteria (Bishop et al, IN: Standard Methods for the Examination of Dairy Products, 347–395, 1992, 16th Edition, R. T. Marshall, ED., American Public Health Association, Washington, D.C.).

Rapid methods are needed to screen for the presence of trace levels of specific antibiotics or a class of antibiotics in biological fluids and tissues. Enzyme immunoassay techniques have been used only to a limited extent for detection of veterinary drugs due to the lack of sensitivity needed for detection at tolerance or safe levels. The high specificity of immunoassays also limits the number of compounds that can be analyzed compared to a broad spectrum detection obtainable using microbial inhibition assays. Production of antibodies with desired specificities and affinities is time consuming. There are various methods for detection of aminoglycoside antibiotics in biological fluids. Yao et al (J. Antibiotics (TOKYO), Vol.37 (11), 1462–1468, 1984) report a technique useful in the identification, quantification, and screening of aminoglycosides using a heterogeneous microplate enzyme immunoassay with a sensitivity of 10 pg/ml (1 pg/assay) toward gentamicin. Aminoglycoside antibiotics, such as sisomicin, forimicin B, seldomycin, tobramycin, kanamycin A, kanamycin B, spectinomycin, apramycin, hygromycin B, butirosin, streptomycin, paromomycin, validamycin A, sorbistin B, streptothricin, and neomycin A; in fermentation broths were detected by the method. Purified gentamicin antibody is coated onto the surface of wells of a microtiter plate and incubated with gentamicin-alkaline phosphatase conjugate. The amount of enzyme bound to the antibody was quantified by measuring the change in absorbance at 410 nm after the addition of the substrate, p-nitrophenyphosphate. Competitive assay performed by incubating the antibody and enzyme conjugate with various aminoglycosides showed that the antibody probe cross-reacted with all aminoglycosides tested, except neomycins B and C. No cross-reaction was detected with non-aminoglycoside antibiotics.

The analysis of spectinomycin in foods includes chromatographic methods utilizing ion pair solid phase extraction, HPLC separation followed by post column derivatization and fluorescent detection of its 2-naphthalenesulfonyl chloride (NSCl) derivatives. The sensitivity of the liquid chromatographic method is 4 ng per sample load (Tsuji et al, J. Chromatography, Vol. 333, 365–380, 1985). A high performance liquid chromatographic (HPLC) method is reported for detection in turkey plasma at 1.42 ppm (Burton et al, J. of Chromatography, Vol. 571, 209–216,1991) and in swine, chicken, and calf plasma at 50 ppm (Haagsma et al, J. Chromatography, Biomedical Applications, Vol. 615, 289–295, 1993). The tolerance level for spectinomycin residue is 100 ppb in uncooked edible tissues in chickens. The use of *Bacillus stearothermophilus* and a 65° C. incubation yielded a rapid assay with a sensitivity of 0.2 micrograms per gram of egg (Katz et al, J. Assoc. Off. Anal. Chem., Vol. 61(5), 1103–1106, 1978). The official method for detection of spectinomycin is a microbial turbidimetric assay with an LDL (lowest detectable level) of 2.8 ppm in all tissues of all species (NADA 47–244, New Animal and Drug Application, Upjohn Company, Kalamazoo, Michigan). The analytical range for this assay is 24 to 37.5 ppm. Therefore, a rapid method with higher sensitivity than the microbiological turbidimetric assay is needed to rapidly screen for the presence of spectinomycin at ppb levels.

There are various methods for purification of aminoglycosides from biological fluids. U.S. Pat. No. 4,729,951 (Fereczy et al) discloses a detection and quantification method for determining the presence of aminoglycosides in fermentation broth using thin-layer chromatography. The antibiotic composition is determined by using silica gel as adsorbent and a 1:1:1 mixture of ethanol, methyl-ethyl ketone, and 25 percent aqueous ammonium hydroxide as developing solvent. 0.1 to 0.5 μg/ml portions of the aminoglycoside solution is spotted onto the plates. After drying, a medium containing *Bacillus subtilis* is layered over the surface of the plate which is subsequently incubated at 37° C. for 16 hours. The size of the inhibition zones is measured and compared to a standard.

U.S. Pat. No. 4,482,707 (Sakakibara et al) discloses a purification method for saccharocin, an aminoglycoside antibiotic, produced by a fermentation process. Culture broth is adjusted to acidic pH, neutralized, and filtered to obtain a filtrate. The active principles are adsorbed on an ion-exchange resin after passing the culture filtrate through a column of the same. The active principles are eluted by 1N aqueous ammonia, and the eluate is concentrated. After adjusting the pH, the concentrate is passed through a column of CM-sephadex C-25 ($NH_4^+$type) to adsorb the active principles, and the column is eluted with 0.03N aqueous ammonia.

While there are various methods for detecting aminoglycoside antibiotics in the animals, there still remains a need in the art for a rapid, cost effective detection method. Furthermore, there still remains a need in the art for a rapid, cost effective method for purifying aminoglycosides. Finally, there remains a need in the art for a rapid method for the removal of aminoglycosides from biological fluids such as milk. The present invention is different from prior art methods and provides for a non-immunoaffinity chromatography method for detecting, purifying, and removing aminoglycosides from biological materials.

SUMMARY OF THE INVENTION

It is therefore an object of the present invention to provide a method for detecting aminoglycosides in biological samples that includes a step of contacting a biological sample with an immobilized aminoglycoside binding protein.

Another object of the present invention is to provide a method for detecting aminoglycosides in biological samples wherein the aminoglycoside is captured by immobilized lysozyme or α-lactalbumin.

A still further object of the present invention is to provide a method for removing aminoglycosides from edible biological samples that includes a step of non-immunoaffinity chromatography wherein the aminoglycoside is captured by immobilized lysozyme or α-lactalbumin.

Another object of the present invention is to provide a method for purifying aminoglycosides that includes a step of non-immunoaffinity chromatography wherein the aminoglycoside is captured by immobilized lysozyme or α-lactalbumin.

Further objects and advantages will become apparent from the following description.

DETAILED DESCRIPTION OF THE INVENTION

Figure 1:
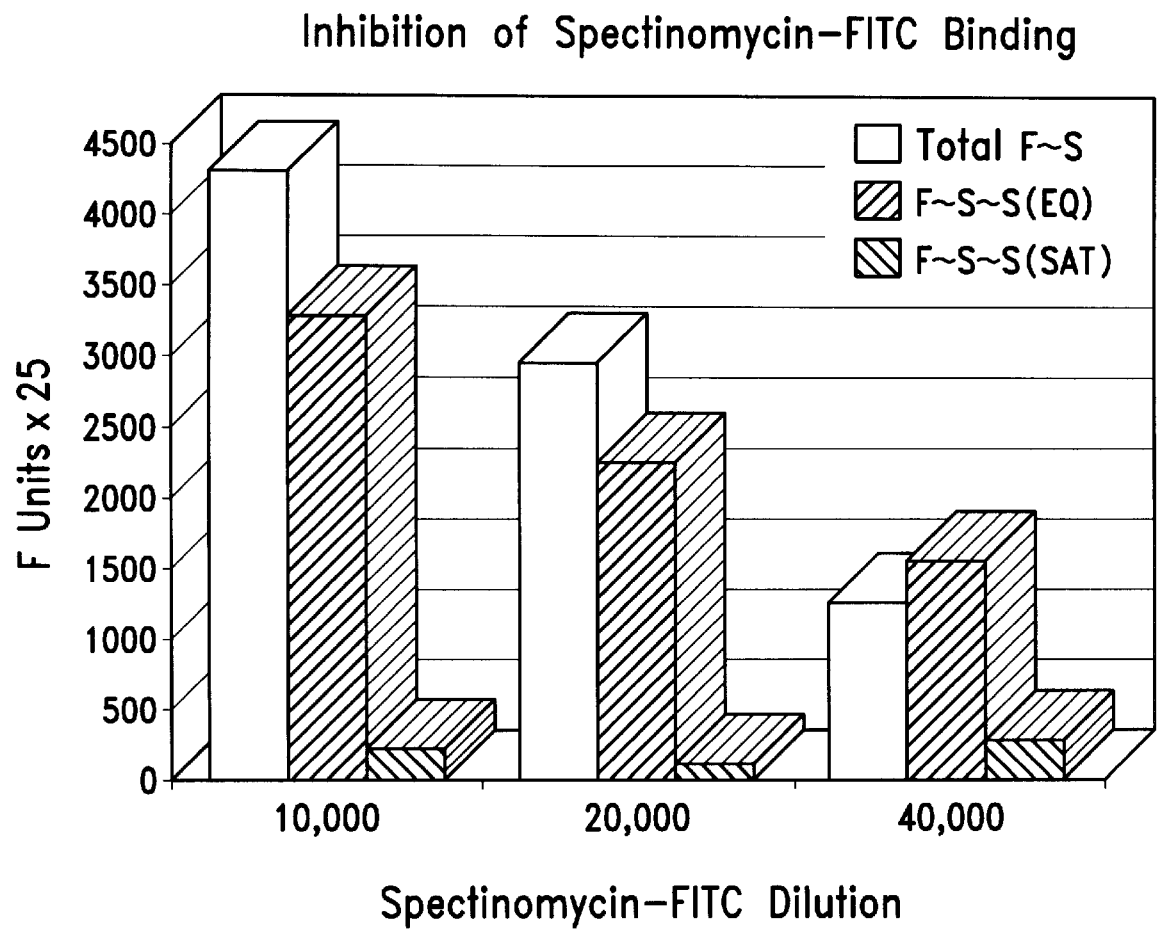
FIG. 1 is a bar graph depicting inhibition of spectinomycin-FITC binding comparing a 1-step equilibrium assay to a 2-step saturation assay.

The aminoglycoside antibiotics consist of a group of related antibiotics containing aminosugar residues and aminocyclitol. The primary biological effect of the aminoglycoside antibiotics is the inhibition of protein synthesis in microorganisms and mammalian cells. The subject invention is a non-immunological binding method for the detection and purification of aminoglycosides or removal of aminoglycosides in biological fluids. It requires specific recognition of a molecule for a ligand. The method is rapid and relatively inexpensive and reusable. Lysozyme and α-lactalbumin are enzymes that both bind saccharide substrates. However, lysozyme catalyzes the hydrolysis and α-lactalbumin catalyzes the synthesis of $\beta(1\rightarrow4)$ glycosidic linkages. Covalent enzyme-substrate adducts of lysozyme have a distorted covalently linked sugar ring. The distortion of substrate toward a transition state is probably important for lysozyme catalysis. The aminoglycoside antibiotics bind to the two proteins but no reaction occurs because of the absence of a $\beta(1\rightarrow4)$glycosidic bond in the antibiotic molecule. There is a close structural similarity between lysozyme and α-lactalbumin suggesting that the genes for α-lactalbumin and lysozyme were derived from a common ancestor. This is supported by the weak lysozyme-like activity present in α-lactalbumin (White et al, Anal. Biochem., Vol. 212, 263–268, 1993). Although the two proteins have different substrate specificities and different isoelectric points, some of the residues in lysozyme which interact with substrates are conserved in α-lactalbumin (Brew et al, J. Biol. Chem., Vol. 242, 3747–3749, 1967). Lysozyme is a basic protein (pI 11), whereas α-lactalbumin is an acidic protein (pI 4.5). The overall charge of the protein is related to the enzymatic role. The described novel methods for detecting and purifying aminoglycosides is important because a rapid and a more specific method for detecting and purifying aminoglycosides is needed compared to microbial inhibition assays and specific prior art purification techniques. Furthermore, the present method allows for a rapid screening and assay of a broad class of chemical compounds as compared to the high specificity of immunoassays which limits the number of compounds that can be analyzed.

The term aminoglycoside encompasses, for example, apramycin, amikacin, spectinomycin, streptomycin, hygromycin A, hygromycin B, neomycin, gentamicin, dihydrostreptomycin, tobramycin, amikacin, kanamycin, nalidixic acid, nitrofurantoin, colistimethate, lincomycin, amphotericin B, flucytosine, their metabolites and derivatives.

Broadly, one method of the present invention comprises the step of immobilizing either lysozyme or α-lactalbumin (protein) onto a solid carrier, adding the immobilized protein to 5 ml disposable columns, and activating the immobilized lysozyme with 0.1M NaOH. Immobilized α-lactalbumin does not require activation for binding of the aminoglycosides. Aqueous samples are applied to the column at a flow rate of 1 ml/min. The aminoglycoside content of the eluates is then detected using an assay that is commensurate with the label employed.

In another embodiment of the present invention, lysozyme or α-lactalbumin are immobilized onto a solid carrier. Aqueous sample and standards are added to microtiter wells or microtubes followed by the addition of the carrier-immobilized enzyme. The mixture is incubated for approximately about 20–30 minutes followed by the addition of a label. This is incubated for approximately 30–45 minutes. The unbound label is separated by filtration or other appropriate means. The assay is read according to the type of label employed.

In another embodiment, an aminoglycoside is immobilized on a solid carrier and lysozyme or α-lactalbumin is labeled and samples are assayed for the presence of aminoglycosides. The utilization of aminoglycoside-lysozyme or α-lactalbumin interactions in competitive binding assays for detection of aminoglycosides can also use methods that do not require labels such as surface plasmon resonance (SPR) (Fagerstam, A Non-Label Technology for Real-Time Biospecific Interaction Analysis, IN: Techniques in Protein Chemistry II, Villafranca, J.(editor), Academic Press Inc., New York(1990), which is herein incorporated by reference) and piezoelectric biosensors, for example.

To provide detection capability, the samples are suitably labeled by a label which is any detectable functionality, such as, for example, radioactive, enzymatic, fluorescent, luminescent, or organic labels. Examples of labels include radioisotopes $^{32}P$, $^{14}C$, $^{125}I$, $^{131}I$, and $^{3}H$ for example; fluorophore such as fluorescein and derivatives such as fluorescein isothiocyanate, cyanine dyes, rhodamine, bodipyl, cascade blue, phycoerythrins, Texas red, fluorescent producing enzyme substrates, laser induced fluorescent dyes, BCECF, SNAFL and fluorescamine for example; and enzymes such as horseradish peroxidase, lactoperoxidase, microperoxidase and alkaline phophatases, for example; chromophores, spin labels, chemiluminescent labels, ligands having specific binding partners such as biotin/avidin; bacteriophage labels, stable free radicals, or any other labels that may interact with each other to enhance, alter, or diminish a signal. Labeling procedures are dependant upon the label selected and are well known to the skilled artisan. Preferred labels are fluorescent labels such as fluorescein isothiocyanate, Isomer I 98% (FITC) or fluorescamine. The samples can be visualized by thin layer chromatography, for example; or quantified using a fluorometer, a Fluorescent Concentration Analyzer (FCA) Idexx, Inc., Westbrook, Me.) or a fluorescent reader, for example.

The enzymes are immobilized on solid carriers. Non-limiting examples of solid carriers useful in the present invention are agarose, latex, chitin, alginate, cellulose, silica, metal oxides, polystyrene, other polymers, and derivatives thereof. Preferred carriers are N-hydroxysuccinimide ester agarose and carboxylated latex particles.

To determine the per cent of immobilization of lysozyme or α-lactalbumin on the solid carrier, a Biorad assay is performed and the concentration of protein content in the supernatant of washed particles is compared to the initial protein content added to the particle for binding. Samples and standards (20 μl) are transferred to microtiter wells and 100 μl of Biorad reagent is added. The absorbance is determined after approximately 5 and 10 minutes at 595 nm. The sample concentration is calibrated from 0, 0.125, 0.025, 0.05, and 0.1 mg/ml of lysozyme standard.

The term aqueous sample is defined to mean any biological sample from which aminoglycosides can be detected. Non-limiting examples of such samples include serum or plasma samples, animal tissue homogenates, deproteinized tissue homogenates, milk, raw egg, fermentation broths, animal feeds, and marine feeds.

The following examples illustrate the invention. They are intended to further illustrate the invention and are not intended to limit the scope as defined by the claims.

EXAMPLE 1

This example illustrates the development of an aminoglycoside competitive binding assay using spectinomycin as the test aminoglycoside to confirm the presence of aminoglycosides in aqueous tissue extracts. Lysozyme is immobilized onto latex particles using the following method. Carboxylated latex particles are dispersed by sonication, 10 pulses of 75% duty cycle using power 3. Aliquots of 0.2 ml particles are transferred into 10 ml conical polypropylene tubes. The carboxyls are activated by adding 150 mg N-ethyl-N$^3$(3-dimethylaminopropyl)-carbodiimide hydrochloride (EDC) and allowed to stand for approximately 15–20 minutes at approximately room temperature. Two ml of 0.1 mg/ml lysozyme in pH 7, 0.1M phosphate buffer is heated at 370° C. for approximately 30 minutes and then is added to the activated particles drop by drop while mixing gently. The mixture is incubated at 37° C. for approximately 1.5 hours. The derivatized latex (latex-lysozyme) is centrifuged at approximately 8225×g (approximately 10,000 rpm) for approximately 5 minutes at approximately 4° C. The supernatant is assayed for protein content and compared with initial protein concentration using a Biorad protein assay. The latex-lysozyme is washed twice with 2 ml of pH 7 phosphate buffer and centrifuged at approximately 3,000×g for approximately 10 minutes. Four ml of phosphate buffer containing 0.1% sodium azide and 0.015% Brij surfactant is added to the latex lysozyme and the mixture is sonicated with 10 pulses prior to storage at 4° C.

To prepare the label for the assay, spectinomycin base (0.01 mM) and FITC (0.02 mM) are dissolved separately in 0.5 ml of 10 mM dibasic phosphate buffer adjusted to pH 8.8 with 10 mM monobasic phosphate buffer. The mixture is mixed gently for 2 hours at room temperature prior to storage at 4° C. The labeling is carried out in brown vials or in tubes wrapped with aluminum foil to prevent photodegradation of the fluorescent compounds. Dilutions are made such that 20 μl contains approximately 5 ng spectinomycin-FITC. Completion of derivatization is screened by thin layer chromatography using 10 ml of developing solvent, methanol:chloroform:acetone:ammonium hydroxide in a ratio of 3:3:3:1. The reaction mixture is diluted in distilled water, 1:100, and applied in 1 μl quantities to TLC plates and developed for approximately 10 minutes in a 118 ml capacity round glass bottle. The derivatized compound is compared to a 0.1 μM FITC sample. These TLC conditions are also used to purify spectinomycin-FITC derivatives when derivatization is not complete using Whatman Channeled TLC plates. The spectinomycin-FITC bands are scraped and extracted with phosphate buffer, pH 6.

Binding and competition interactions are assessed using lysozyme-particles containing 0.6 pg protein in 10 μl. Spectinomycin-FITC (20 μl), diluted approximately 1:10, 000 (245 ng/ml), 1:20,000 (122 ng/ml), and 1:40,000 (61 ng/ml) is incubated with the lysozyme-particles for approximately 30 minutes (FIG. 1). The effects of two binding modes, 1-step and 2-step binding, is compared. In a 1-step equilibrium binding assay, the labeled and unlabeled spectinomycin are incubated for approximately 30 minutes simultaneously with the lysozyme-particle. In the 2-step saturation binding assay, the displacement of the bound spectinomycin-FITC is determined by adding unlabeled spectinomycin, 20 µl of 100 ng/ml, after the 30 minute incubation with spectinomycin-FITC. The reaction mixture is further incubated for an additional 30 minutes. This evaluation demonstrates that the spectinomycin-FITC has fluorescent signals that proportionally decrease as its concentration was reduced. The spectinomycin-FITC at 61 ng/ml (1:40,000 dilution) is detectable at 25×gain. These responses are linear from 4.9 ng (20 µl of 245 ng/ml) to 1.2 ng (20 µl of 61 ng/ml) and indicates that less spectinomycin-FITC is captured by the lysozyme-particles when present at lower concentrations. The addition of 20 ng spectinomycin to the lysozyme-particle and spectinomycin-FITC complex results in displacement of the bound spectinomycin-FITC at the higher concentrations of 4.9 ng and 2.45 ng. This displacement or competition for the binding sites is greater (96%) in a 2-step assay compared to a 1-step equilibrium assay (34%). However, dilute amounts of spectinomycin-FITC (1.22 ng) is not displaced in a 2-step assay but the unlabeled drug competed for 78% of the binding sites in the 1-step equilibrium assay. These interactions suggest that this assay can be used for trace level analysis, below 10 ppb, of aminoglycoside using a 2-step assay and utilizing tracer concentrations of 2.5 ng or greater, per test.

EXAMPLE 2

The assay of example 1 is used to determine the dose response of spectinomycin and the presence of spectinomycin in biological samples. Spectinomycin standards are prepared in 10 mM phosphate buffer with 0.1% BSA, pH 6.5 containing 0, 5, 10, 25, 50, and 100 ppb spectinomycin solid. Swine serum samples (1 ml) are deproteinized with an equal volume of acetonitrile and centrifuged at 3,000×g. The acetonitrile in the supernatant is evaporated using a vortex evaporator for approximately 20 minutes. The volumes were adjusted to 0.5 ml with deionized water and 0.5 ml of 10–100 ppb of spectinomycin standards in phosphate buffer is added. Twenty microliters of standards and spiked serum are transferred to Idexx microtiter wells with membrane bottom (Idexx, Inc., Westbrook, Me.). Ten microliters of latex lysozyme-particles (prepared as in Example 1 above) are added and the mixtures are pre-incubated for approximately 20–30 minutes at approximately room temperature. Twenty microliters of spectinomycin-FITC, the tracer, is added and the mixture is incubated for 30–45 minutes. The excess reagent is evacuated with 25 mm Hg for approximately 30 seconds. The wash reagent, 50 µl of phosphate buffer, pH 6.5 containing 0.015% Brij, is manually dispensed into the wells and the buffer is evacuated in the FCA analyzer. All the wells must be free from liquid prior to reading at 485 nm emission and 520 nm excitation.

Figure 2A:
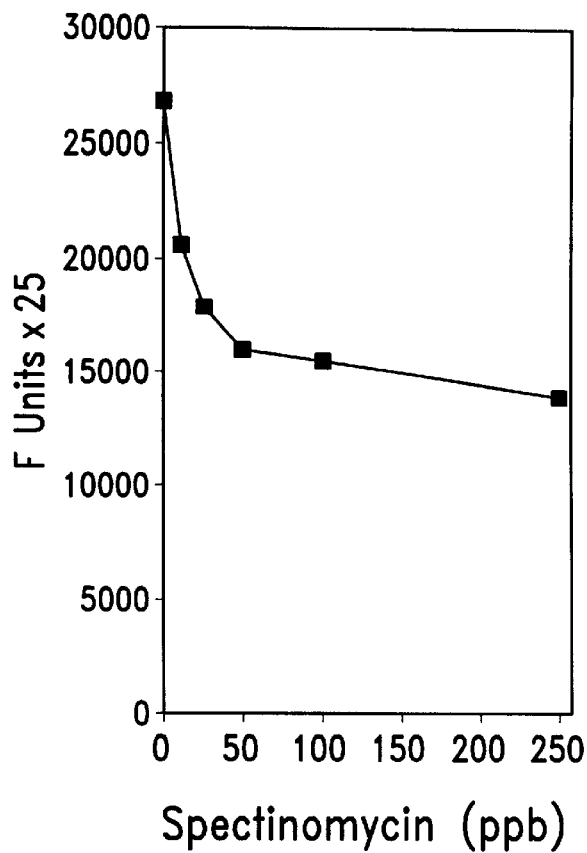
FIG. 2A is a graph showing a 1-step equilibrium assay using 1:10,000 spectinomycin-FITC.
Figure 2B:
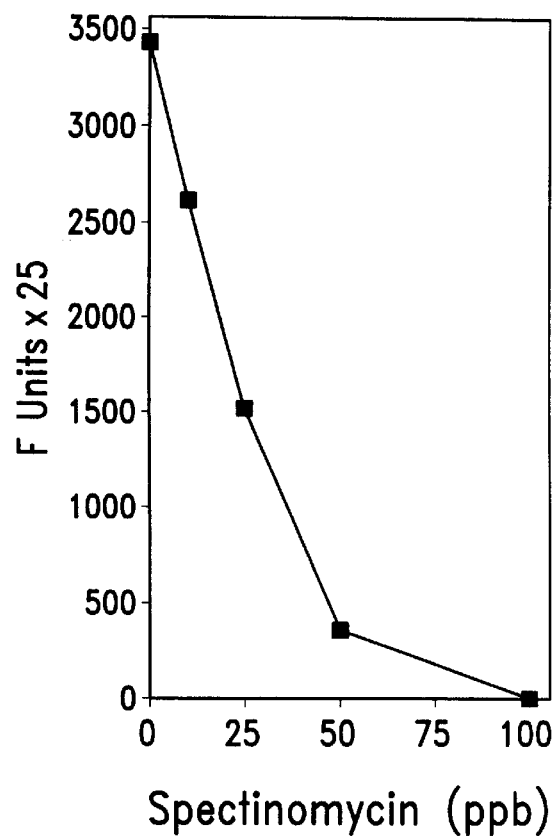
FIG. 2B is a 2-step saturation assay using 1:10,000 spectinomycin-FITC.

The optimized conditions for the assay were determined. The pH of the binding and wash buffers is optimum between approximately 5–6.5. For detection in a range of low parts per billion, each test has a calculated amount of the aminoglycoside, for example, 5 ng spectinomycin-FITC, and 60 mg protein equivalent of lysozyme- or α-lactalbumin-particle. When these conditions are used to determine the binding competition of the unlabeled spectinomycin at 0–250 ppb, the dose response was curvilinear and typical of saturation binding curves (FIG. 2A). A near linear response was indicated at 0–50 ppb (FIG. 2B). The hyperbolic or curvilinear response of the ligand-binding assays indicated multiple binding sites or heterogeneous binding between spectinomycin and lysozyme. The hyperbolic plots show that saturation of the binding sites occur at a concentration where the signal plateau. Therefore, the detection range of the assay is adjusted below the saturation point. Munson and Rodbard (Anal. Biochem., Vol. 107, 220–239, 1980) developed versatile computer programs for the analysis of nonlinear data generated from ligand-binding interactions. However, simple linear transformation of the binding assay data is reported by Chase (Ligand Quarterly, Vol. 2(3), 25–28, 1979; Vol. 2(3), 29, 1979; and Vol. 2(3), 30–33, 1979) plotting the ratio of total over bound signals (T/B) vs concentration of the analyte. This approach is utilized in radioimmunoassay analysis of estradiol and a mean regression correlation ($R^2$) of 0.989 is reported (M. B. Medina, J. Agric. Chem., Vol. 34(6), 1046–1049, 1986, which is herein incorporated by reference). Likewise in this study, the linear transformation of the data in FIG. 2A has an $R^2$ of 0.922 which results from plotting T/B vs 0–50 ppb spectinomycin. In FIG. 2B, the plot of T/B vs 0–50 ppb has an $R^2$ of 0.981. The simple approach of data reduction using this linear transformation is especially suitable when handling small number of samples.

These ligand-binding assays were carried out in 2 binding modes and again, the results of the 2-step incubation assay show higher sensitivity and linearity than a 1-step equilibrium assay. With the biological samples, a deproteinized serum spiked at 1–50 ppb has a near linear response with a correlation coefficient (square root of $R^2$), r=0.962. The analysis of a homogenate of a liver tissue extracted with buffer, centrifuged and prefiltered, was not successful due to clogging of the membranes. The membrane with 1.2 µm pore size and particles with a diameter of 3.6 micron are also utilized. The filtered extracts still resulted in clogged membranes. Therefore, it was concluded that tissues extracts should be deproteinized for analysis by this assay format. However, other approaches for the separation of the "bound" complex from the "free" ligand or tracer can be employed.

Example 1 and Example 2 show that the particle concentration fluorescent assay utilizing the binding protein lysozyme with selectivity for aminoglycosides can be used for trace level analysis of veterinary drug residues. The assay shows a sensitivity below 5 ppb (ng/ml) and can be utilized for quantitative analysis. Forty samples or extracts can be analyzed in duplicate in 30–60 minutes. The assay is simple and rapid with a high throughput and can bridge the gap between microbial assays and chromatographic analysis.

EXAMPLE 3

This example illustrates an affinity chromatography method for the removal of aminoglycosides from biological fluids either for purification of the aminoglycoside or purification of the fluid by removal of aminoglycosides. Lysozyme and α-lactalbumin are immobilized using Affi-Gel 10® (N-hydroxysuccinimide ester agarose gel). A 1 ml aliquot of Affi-Gel 10® is transferred to a 5 ml disposable column, the solvent is drained, and the gel is washed with 3 bed volumes of cold (4° C.) distilled, deionized water. A 2 ml aliquot of lysozyme, 25 mg/ml in 0.1M 3-(n-morpholino)-propanesulphonic acid buffer (MOPS), pH 7.0, is added to the gel within 10 minutes of the water wash. The column is capped, contents mixed to form a uniform suspension, and incubated at 4° C. for 4 hour on a rotator. After incubation, the effluent is collected to determine unbound protein using the BCA® (Bicinchoninic acid, Pierce, Rockford, IL.) method. The remaining active sites on the agarose support are blocked by incubating 1 ml of 0.1M ethylene diamine (in 0.1M MOPS, pH 7.0) with agarose support for 1 hour at 4° C. on a rotator. The gel is washed with MOPS to remove any unbound material ($OD_{280nm}=0$). α-lactalbumin is solubilized in 0.1M MOPS, 80 mM calcium chloride, pH 7.0 and is immobilized on Affi-Gel® using the same procedure described above for lysozyme.

Figure 3:
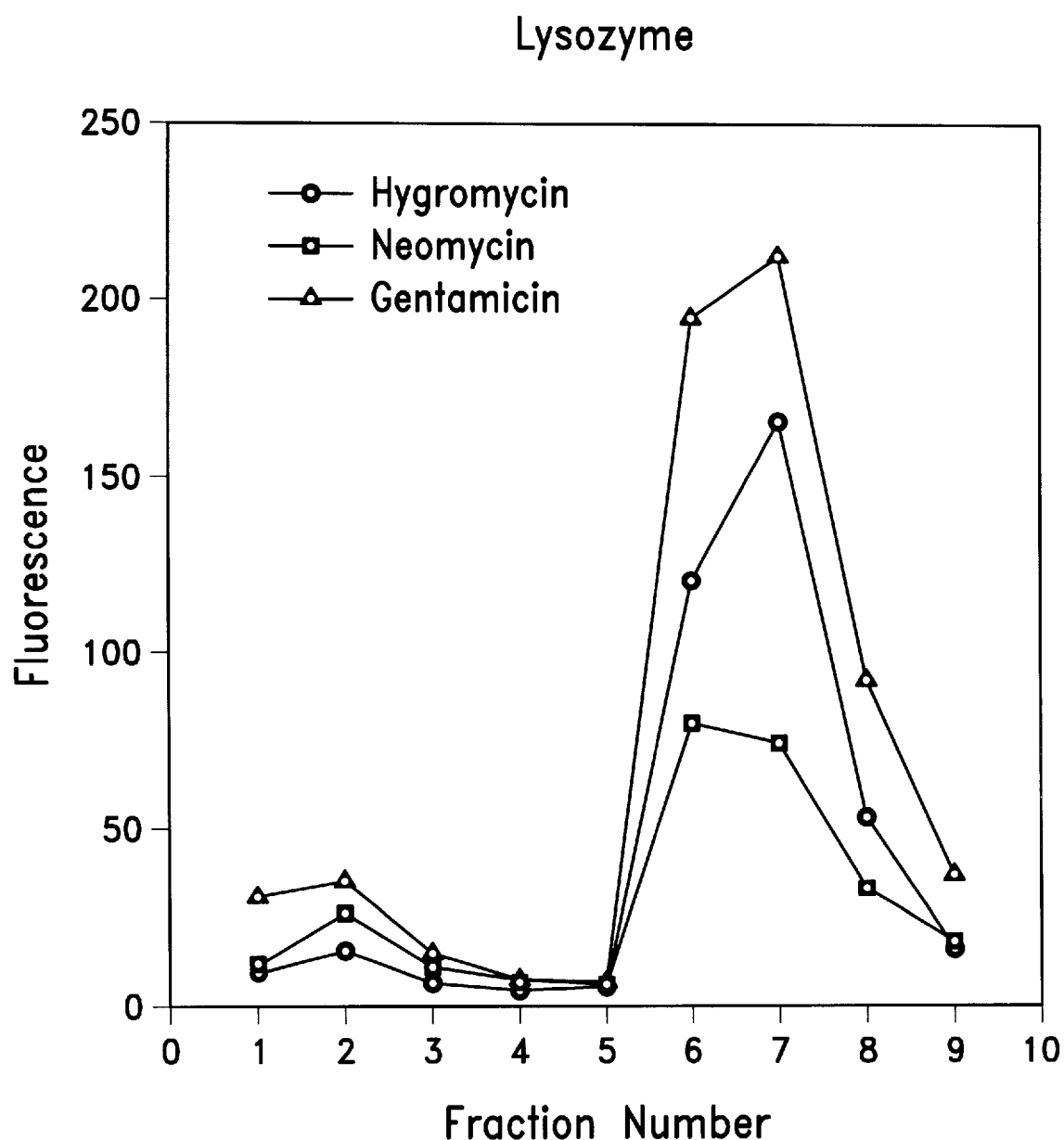
FIG. 3 is a graph showing the elution of aminoglycoside antibiotics from affinity chromatography columns containing immobilized lysozyme.

Affinity columns are prepared by adding 1 ml of agarose gel containing immobilized enzyme to 5 ml disposable columns and draining the solvent. The gel is washed with three bed volumes of cold (4° C.) distilled, deionized water. The immobilized lysozyme is activated by washing the gel with 2 ml of 0.1M NaOH at a flow rate of 1 ml/min followed by 4 bed volumes of cold (4° C.) distilled, deionized water to remove NaOH. Immobilized α-lactalbumin does not require activation for binding of the antibiotics. Aqueous solutions of Hygromycin B, concentrations of 1–100 ppm in distilled deionized water, are applied to the affinity columns and allowed to flow by gravity at approximately 1 ml/min. The flow through was collected to determine the amount of unbound hygromycin B. The columns are washed using four 1.0 ml aliquots of water followed by four 1.0 ml aliquots of 10 mM sodium citrate buffer, pH 4.0. The fluorescence of all fractions are determined as described below. Approximately 29 mg of lysozyme (approximately 53% immobilization efficiency; n=12) and 18 mg of α-lactalbumin (approximately 36% immobilization efficiency; n=7) are immobilized per ml of agarose gel using a 4 hour incubation time. Hygromycin B, neomycin B, and gentamicin at a concentration of 25 ppm in water are completely bound by the immobilized lysozyme and eluted with 10 mM sodium citrate buffer, pH 4.0 (See FIG. 3).

Aminoglycosides can be detected by fluorescence derivatization using fluorescamine (De Silva et al, Anal. Chem., Vol. 47, 714–718, 1975, herein incorporated by reference). The fluorescence assay has a detection limit of 5 ppm for hygromycin B in citrate. Hygromycin B (solubilized in water) at concentrations of 10 ppm (5 ml) and 60 ppm (10 ml) are completely bound by the affinity column and eluted with 10 mM sodium citrate buffer, pH 4.0. The affinity column also binds neomycin B, gentamicin, streptomycin, and dihydrostreptomycin. The fluorescence is detected using a Perkin Elmer luminescence spectrometer at an excitation of 395 nm and an emission of 485 nm. In some cases, TLC analysis (Medina et al, IN Residues of Veterinary Drugs in Food, Haagsma et al ED., Proc. EuroResidue II Conference, Veldhoven, The Netherlands, May 3–5, 1993; J. Chromatography, Vol. 663, 127–135, 1995, both herein incorporated by reference) is performed using the eluate from the affinity columns. The solvent is evaporated from the eluates, the samples reconstituted 1:1 using 95% ethanol, and applied to a Whatman LHK-PD silica gel plate with preabsorbant zones (10×10 cm; 9 lanes). The gel plate is developed for approximately 20 minutes with acetone/ethanol/ammonium hydroxide; 1:1:1, dried in a vacuum oven, cooled to room temperature, and dipped for approximately 4 seconds in 0.02% fluorescamine (acetone/hexane; 1:14). The plate is dried, sprayed lightly with 0.2M sodium citrate buffer, pH 3.0–5.0, with optimal signal at approximately pH 4.0, and the fluorescent bands are detected using an ultraviolet light box at a wavelength of 365 nm. The aminoglycosides show differences in fluorescence intensity upon derivatization using fluorescamine. Fluorescamine reacts with primary amino groups and the aminoglycosides used in this example have differing number of free primary amino groups. Streptomycin and dihydrostreptomycin bind to the lysozyme affinity column; but, they are excluded from further study because of low fluorescence intensity due to the only one free primary amino group. Fluorescamine is used in this study for the evaluation of the affinity chromatography method. There are other derivatization reagents for aminoglycoside antibiotics that have detection limits in the parts per billion range. See Example 2 above.

Figure 4:
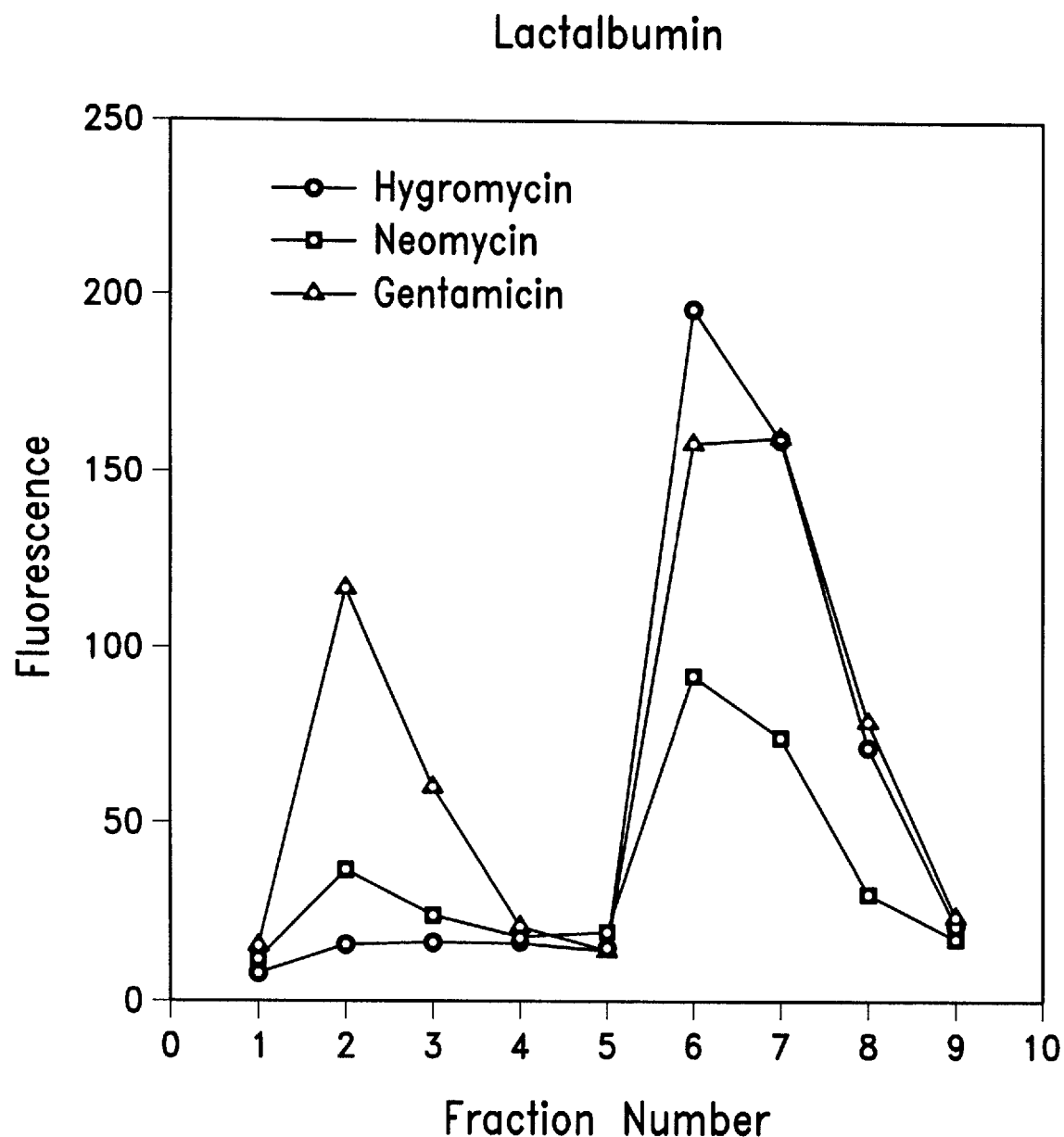
FIG. 4 is a graph showing the elution of aminoglycoside antibiotics from affinity chromatography columns containing immobilized α-lactalbumin.
Figure 5:
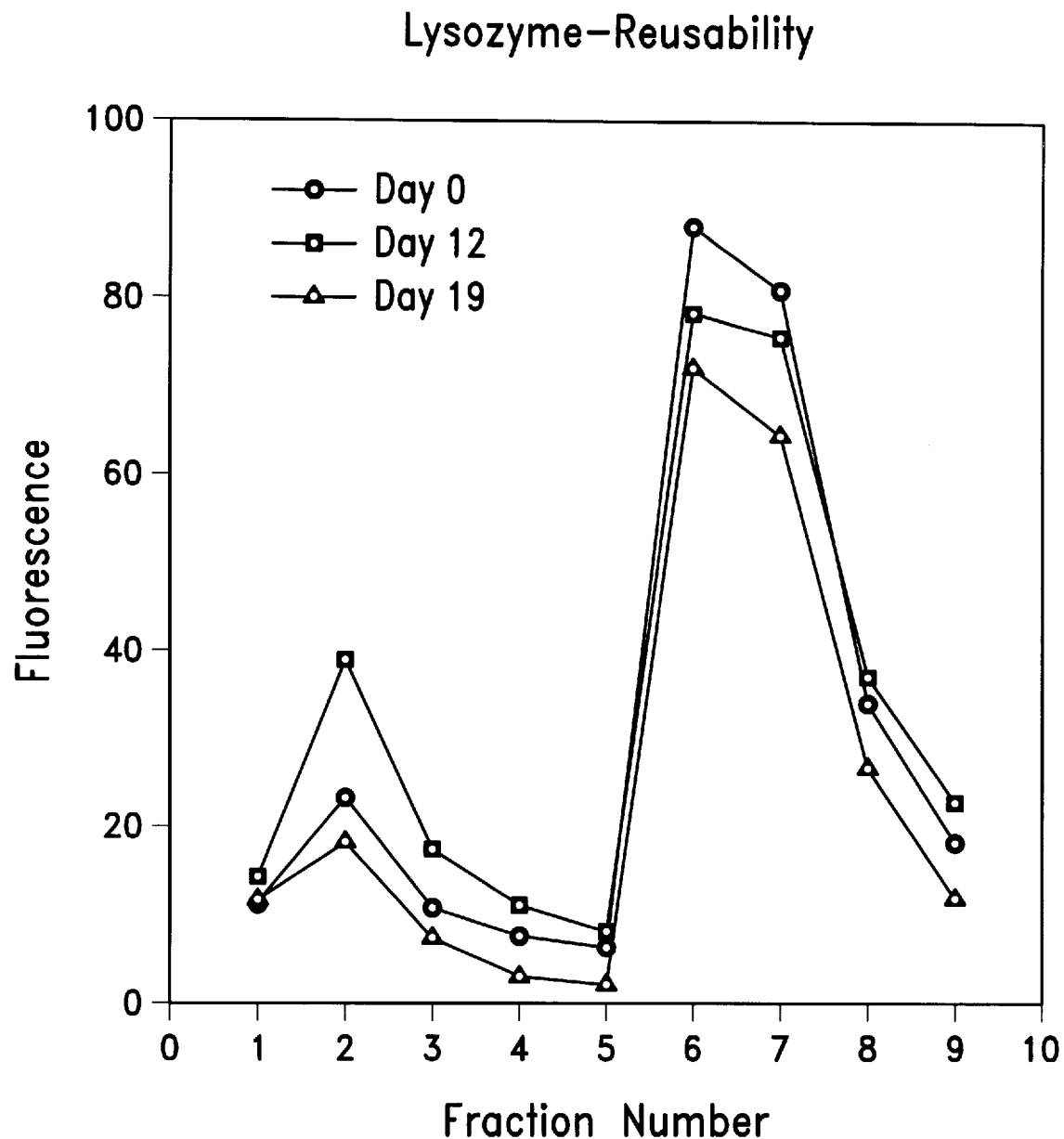
FIG. 5 is a graph showing the elution pattern of neomycin from affinity chromatography columns, containing immobilized lysozyme, prepared and stored for 0,12, and 19 days.
Figure 6:
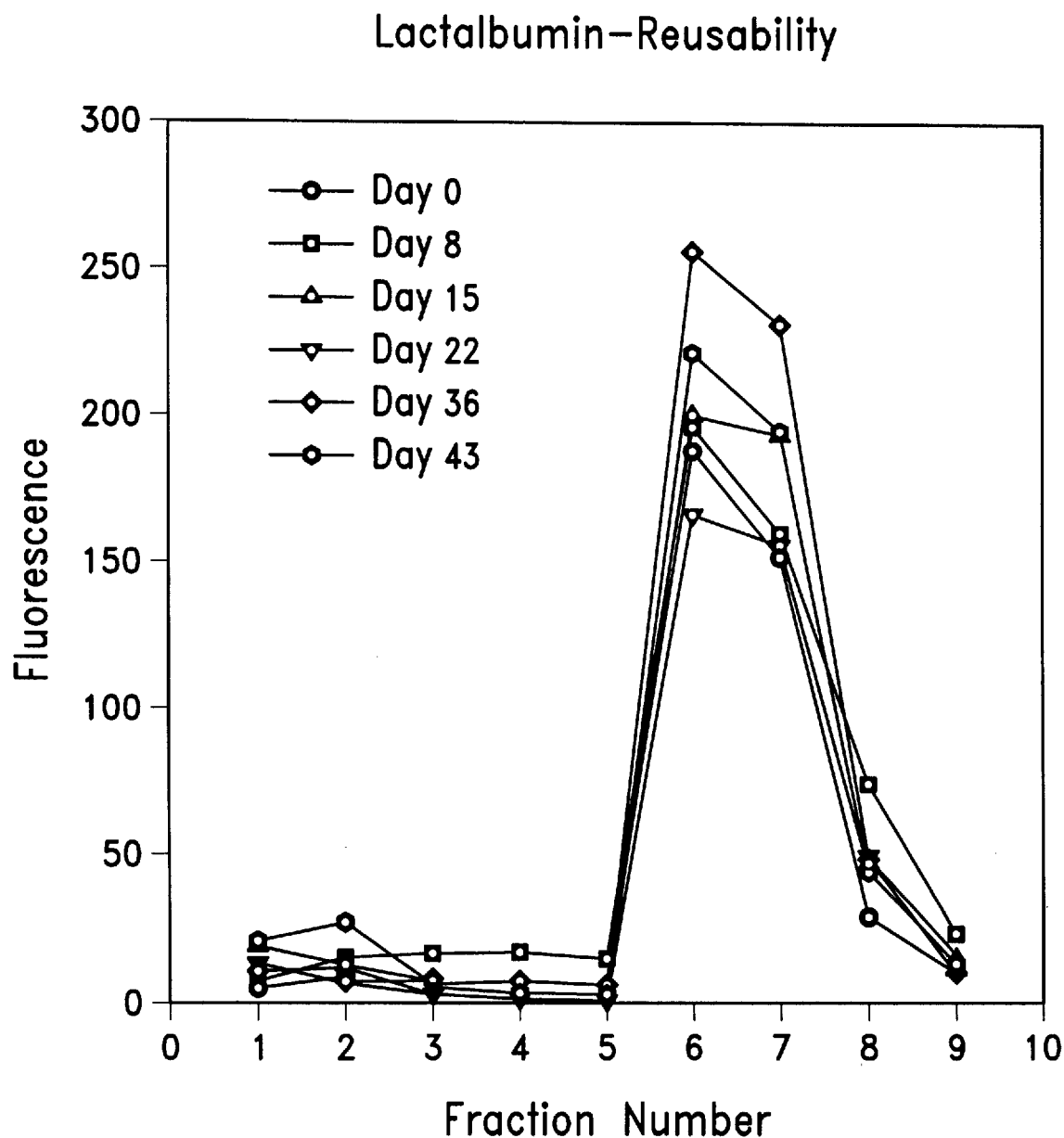
FIG. 6 is a graph showing the elution pattern of hygromycin from affinity chromatography columns, containing immobilized α-lactalbumin, prepared and stored for 0, 8, 15, 22, 36, and 46 days.

Lysozyme has the highest binding capacity for hygromycin B, binding 0.5 mg of hygromycin B per ml of affinity gel. Sodium hydroxide is required for the activation and periodic reactivation of the immobilized lysozyme. Immobilized α-lactalbumin also bound the three aminoglycosides used in this example (See FIG. 4). There is incomplete binding of gentamicin. α-lactalbumin had an overall lower binding capacity, binding 0.1 mg of hygromycin B per ml of affinity gel. This difference (5-fold) can not be totally accounted for based on the total amount of each protein immobilized per ml gel (1.5 fold). The binding mechanism for immobilized α-lactalbumin appears to be ionic in nature but not as strong as for the immobilized lysozyme. The lysozyme and the α-lactalbumin columns show little or no decrease in binding efficiency over a two week period (See FIGS. 5 and 6). The lysozyme columns have decreased binding efficiency for hygromycin on day 12; however, the binding efficiency increased upon reactivation of the immobilized lysozyme using 0.1M NaOH (See FIG. 5). The affinity columns are stored in water at 40° C. and the binding efficiencies show little change after six-month storage.

Hgromycin B in adulterated biological fluids does not bind to immobilized lysozyme due to other ionic species present in the biological samples. Therefore, biological fluids need to be partially deionized prior to affinity chromatography using cation exchange chromatography. The combination of cation exchange and affinity chromatography is used for the detection of hygromycin B in adulterated bovine serum and plasma, swine serum and plasma, and milk samples. The bovine serum samples were spiked with 25 ppm of hygromycin B per ml of sample and the bovine milk was spiked with 250 ppm of hygromycin B per ml of sample. The control samples consisted of either milk or serum without added hygromycin B. The samples are diluted 1:5 using 2% phosphoric acid to acidify them and added to Clean Screen® columns (copolymeric bonded silica with hydrophobic and cationic functions) which are conditioned using a minimum of 2×1 ml aliquots of 5% diethylamine in methanol followed sequentially by water and phosphoric acid prior to sample application. The samples are applied to individual columns at a flow rate of 1 ml/min. Using the same flow rate, the columns are washed using five 1 ml aliquots of water followed sequentially by five 1 ml aliquots of 95% ethanol and five 1 ml aliquots of isopropanol/tetrahydrafuran (2:8). The hygromycin B fractions are eluted using five 1 ml aliquots of 5% diethylamine in methanol. The diethylamine fractions are collected, solvent evaporated using a vortex evaporator, and reconstituted using 1 ml of water. The reconstituted samples are applied to the affinity column (immobilized lysozyme column; described above) and washed sequentially using four 1 ml aliquots of water, four 1 ml aliquots of 95% ethanol, and four 1 ml aliquots of 10 mM sodium citrate buffer, pH 4.0. The citrate fractions were collected for further analysis using direct fluorescence and TLC analysis.

Figure 7:
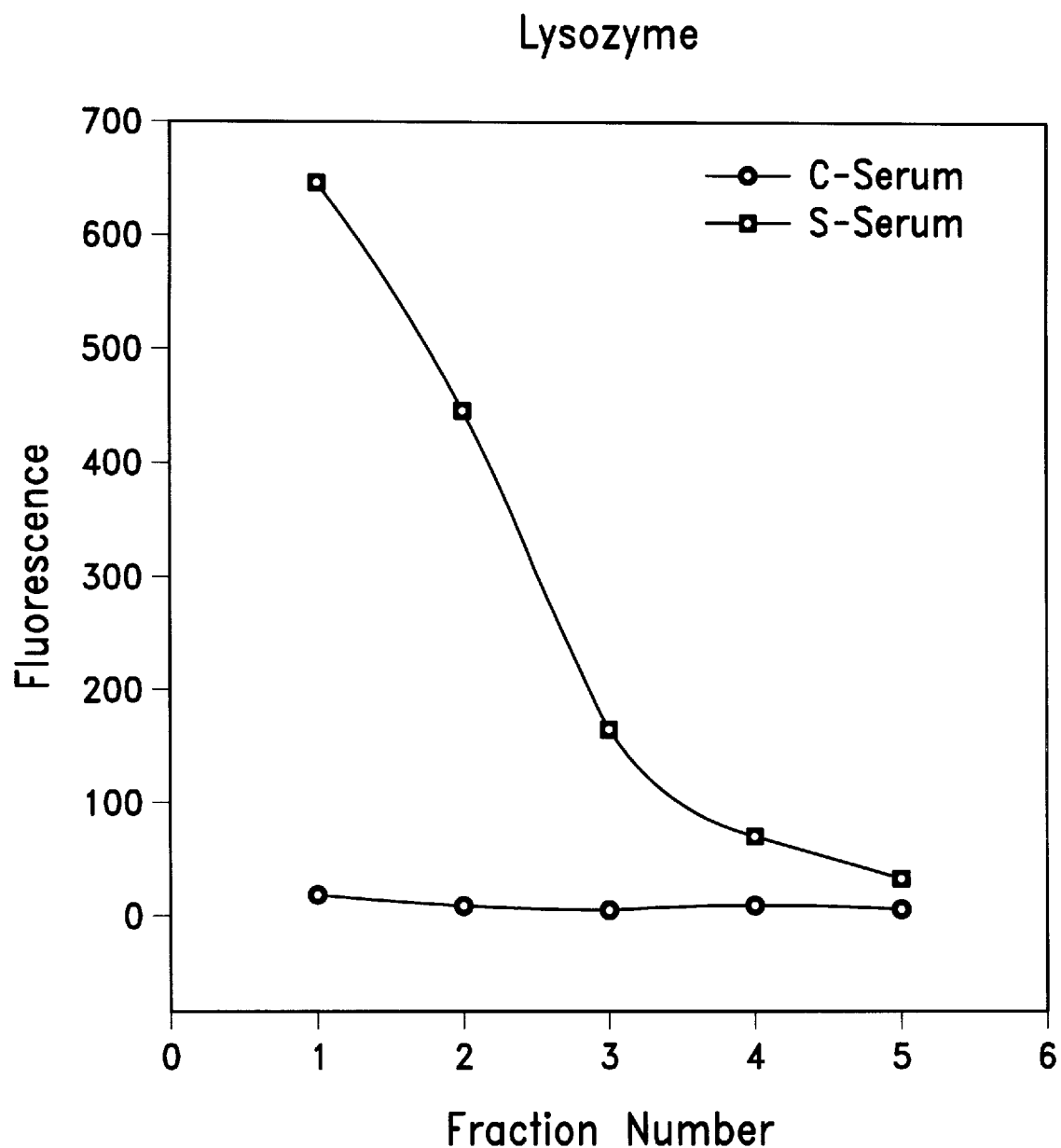
FIG. 7 is a graph showing the elution pattern of hygromycin B in bovine serum using immobilized lysozyme with prior cation-exchange chromatography.
Figure 8:
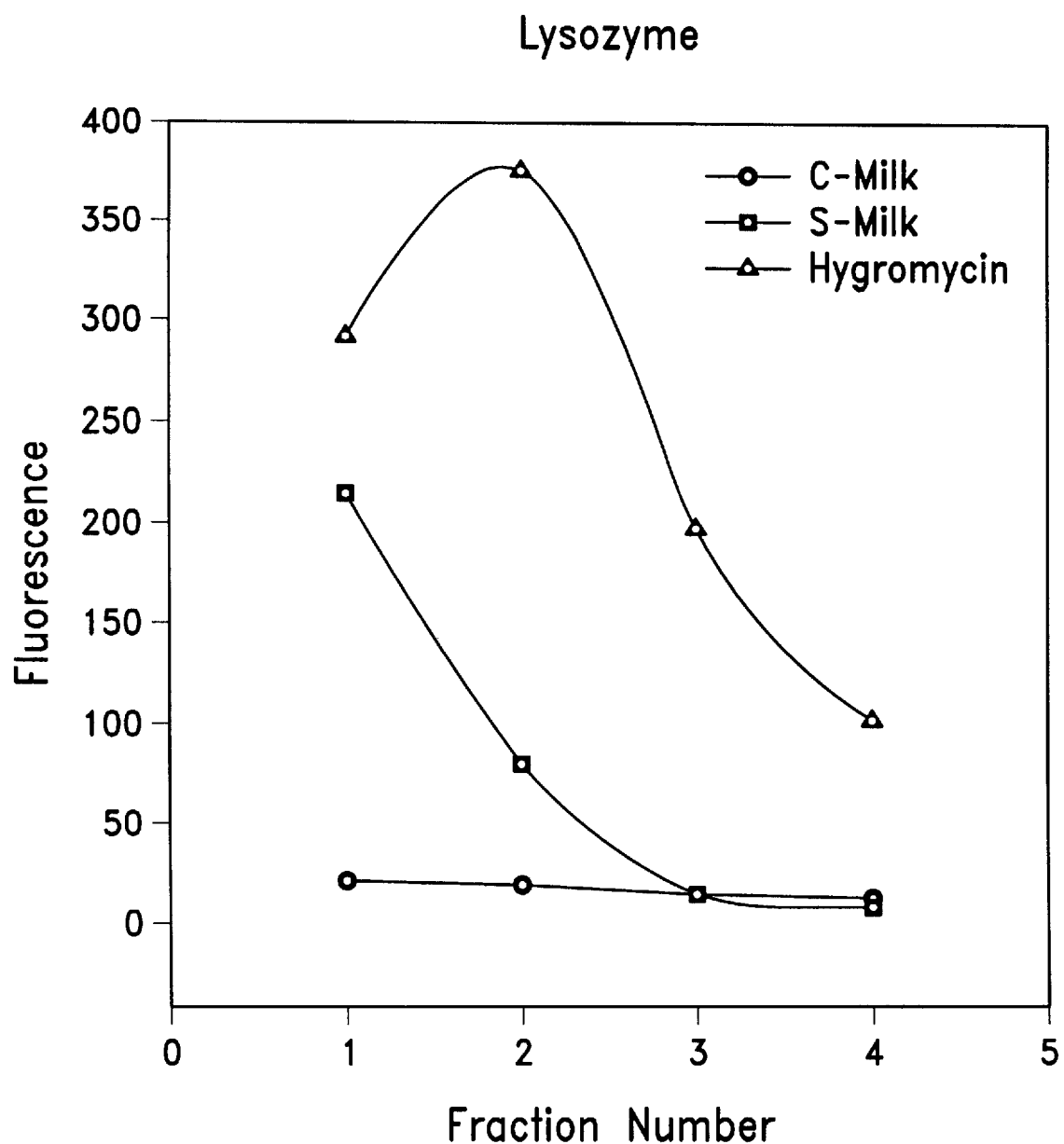
FIG. 8 is a graph showing the elution pattern of hygromycin B in bovine milk using immobilized lysozyme with prior cation-exchange chromatography.

A 0.9 ml aliquot of each of the 1.0 ml fractions is mixed with 0.5 volumes of fluorescamine solution (1 mg/ml in 95% ethanol). The fluorescamine samples are incubated at room temperature for 15 minutes and fluorescence is determined at an excitation of 395 nm and an emission of 485 nm. The control samples (serum and milk blanks without added hygromycin B) show no interfering fluorescent compounds (See FIGS. 7 and 8). The hygromycin spiked serum and milk samples show a high fluorescence intensity. However, the recovery of hygromycin B is incomplete (FIG. 8). This is probably due to hygromycin binding to α-lactalbumin present in the milk. Other preliminary results performed show the binding of hygromycin by immobilized rat albumin. Aminoglycosides are probably bound and transported in vivo by albumins present in blood and milk.

Figure 9:
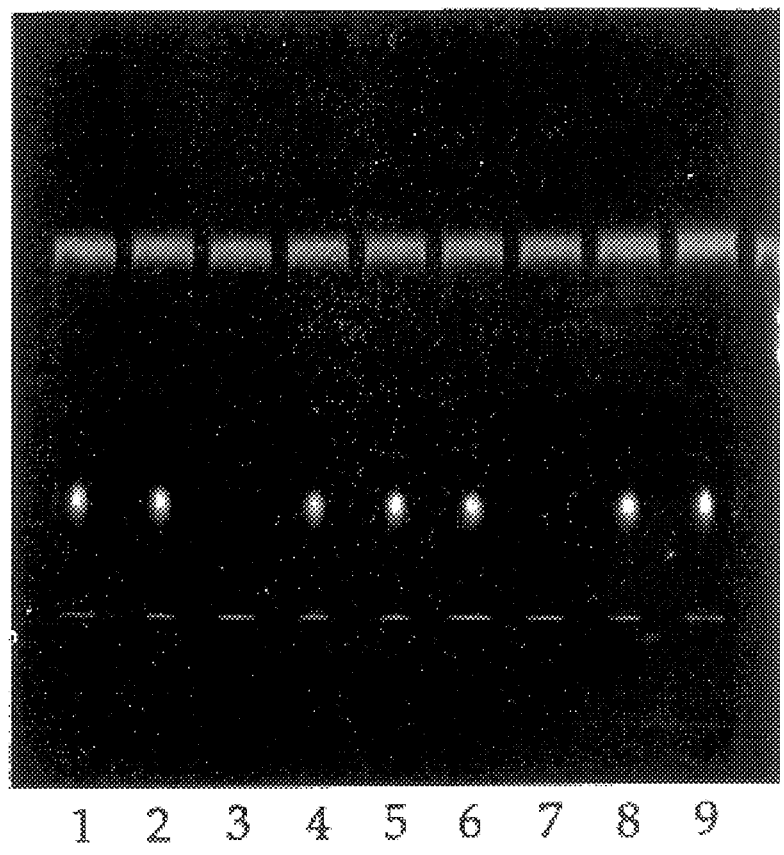
FIG. 9 is a photograph of a TLC plate showing the presence of hygromycin B in fortified bovine serum and water. Lanes 1,5, and 9=standard (25 ppm hygromycin B in water); Lanes 2 and 6=affinity clean-up of hygromycin B in water; Lanes 3 and 7=affinity clean-up of serum control sample (no hygromycin B); Lanes 4 and 8=affinity clean-up of fortified serum sample (25 ppm hygromycin B/ml serum.
Figure 10:
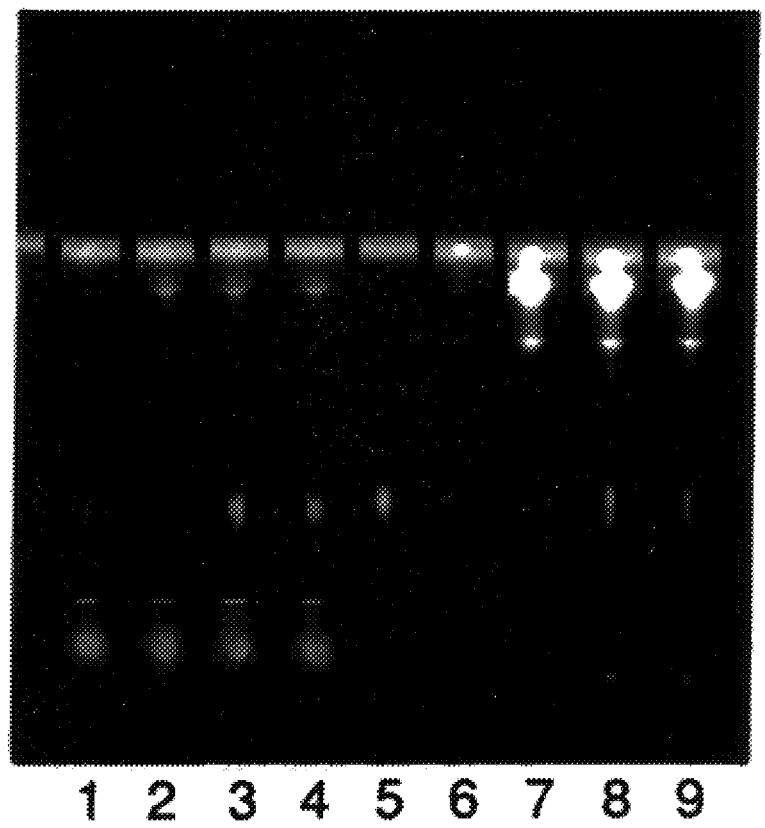
FIG. 10 is a photograph of a TLC plate showing the presence of hygromycin B in adulterated swine plasma. Lanes 1–4 contains deionized and affinity chromatographed samples (Lane 1-hygromycin B, lane 2-plasma blank, lanes 3 and 4-hygromycin spiked plasma). Lanes 6–9 contains deionized samples (lane 6-hgromycin B, lane 7-plasma blank, lanes 8 and 9-hygromycin spiked plasma). Lane 5 contains untreated hygromycin standard (25 ppm).

Hygromycin B is detected in bovine serum using the same procedure followed by TLC analysis (See FIG. 9). The remaining 0.1 ml aliquot of each 1.0 ml citrate fraction is used for TLC analysis using the method of Medina et al (Euro-Residues II Conference Proceedings, supra). The solvent is evaporated from the 0.1 ml eluates using a vortex evaporator and the samples are reconstituted 1:1 using 95% ethanol. The TLC analysis is performed as described in Medina et al (Euro-Residues II, above). Lactalbumin affinity chromatography of hygromycin B from adulterated biological fluids did not achieve complete purification of hygromycin B. However, the purification was sufficient for identification of hygromycin after TLC analysis. TLC analysis shows less interfering fluorescent matter using a combination of deionization and affinity chromatography (See FIG. 10).

The foregoing description is for the purpose of illustration. Such detail is solely for that purpose and those skilled in the art can make variations therein without departing from the spirit and scope of the invention.

We claim:

1. A method for detecting aminoglycosides in biological samples comprising binding an aminoglycoside binding protein selected from the group consisting of lysozyme and α-lactalbumin to a solid carrier to form a bound protein, contacting a sample containing amino glycosides with said bound protein to form a first mixture, incubating said first mixture for a first time period, adding a label to said first mixture to form a second mixture, incubating said second mixture for a second period of time to form a labeled sample, and measuring the label in said labeled sample to determine the presence of aminoglycosides.

2. The method of claim 1 wherein said solid carrier is particles made up of materials selected from the group consisting of latex, agarose, cellulose, metal oxides, chitin, alginate, silica, polystyrene, and derivatives thereof.

3. The method of claim 2 wherein said particle is made up of carboxylated latex.

4. A method for detecting and removing aminoglycosides from a biological sample comprising contacting a sample containing aminoglycosides with an aminoglycoside binding protein selected from the group consisting of lysozyme and α-lactalbumin immobilized on a solid carrier to form a first complex of aminoglycosides bound to said binding protein, removing said first complex from said sample, removing said aminoglycosides from said binding protein to form a second sample, adding a label to said second sample from a second complex of said label bond to said aminoglycosides, and measuring said label to determine the presence of aminoglycosides in said sample.

5. A method for removing aminoglycosides from a biological sample comprising adding a sample containing aminoglyesides to a bioreactor containing an aminoglycoside binding protein selected from the group consisting of lysozyme and α-lactalbumin immobilized on a solid carrier, passing said sample through said reactor to bind said aminoglycosides to said protein in order to remove the aminoglycosides from said sample, and collecting said biological sample wherein said sample is aminoglycoside-free.

6. The method of claim 4 or 5 wherein said solid carrier is particles made up of materials selected from the group consisting of latex, agarose, cellulose, metal oxides, chitin, alginate, silica, polystyrene, and derivatives thereof.

7. The method of claims 1 or 4 wherein said label is selected from the group consisting of $^{32}P$, $^{14}C$, $^{125}I$, $^{132}I$, $^{3}H$, fluorescein isothiocyanate, fluorescamine, horseradish peroxidase, microperoxidase, alkaline phosphatase, and avidin/biotin complex.

8. The method of claim 1, 4, or 5 wherein said biological sample is milk.

9. The method of claim 1, 4, or 5 wherein said biological sample is a fermentation broth.

10. The method of claim 5 wherein the biological sample is selected from the group consisting of a fermentation broth and milk.

11. The method of claim 10 wherein said sample is a fermentation broth and said immobilized binding protein with bound aminoglycosides is removed from said reactor and the aminoglycosides are eluted from said protein.

* * * * *